Oct. 13, 1931. F. SPANBAUER Plant Pat. 2
ROSE
Filed July 1, 1930
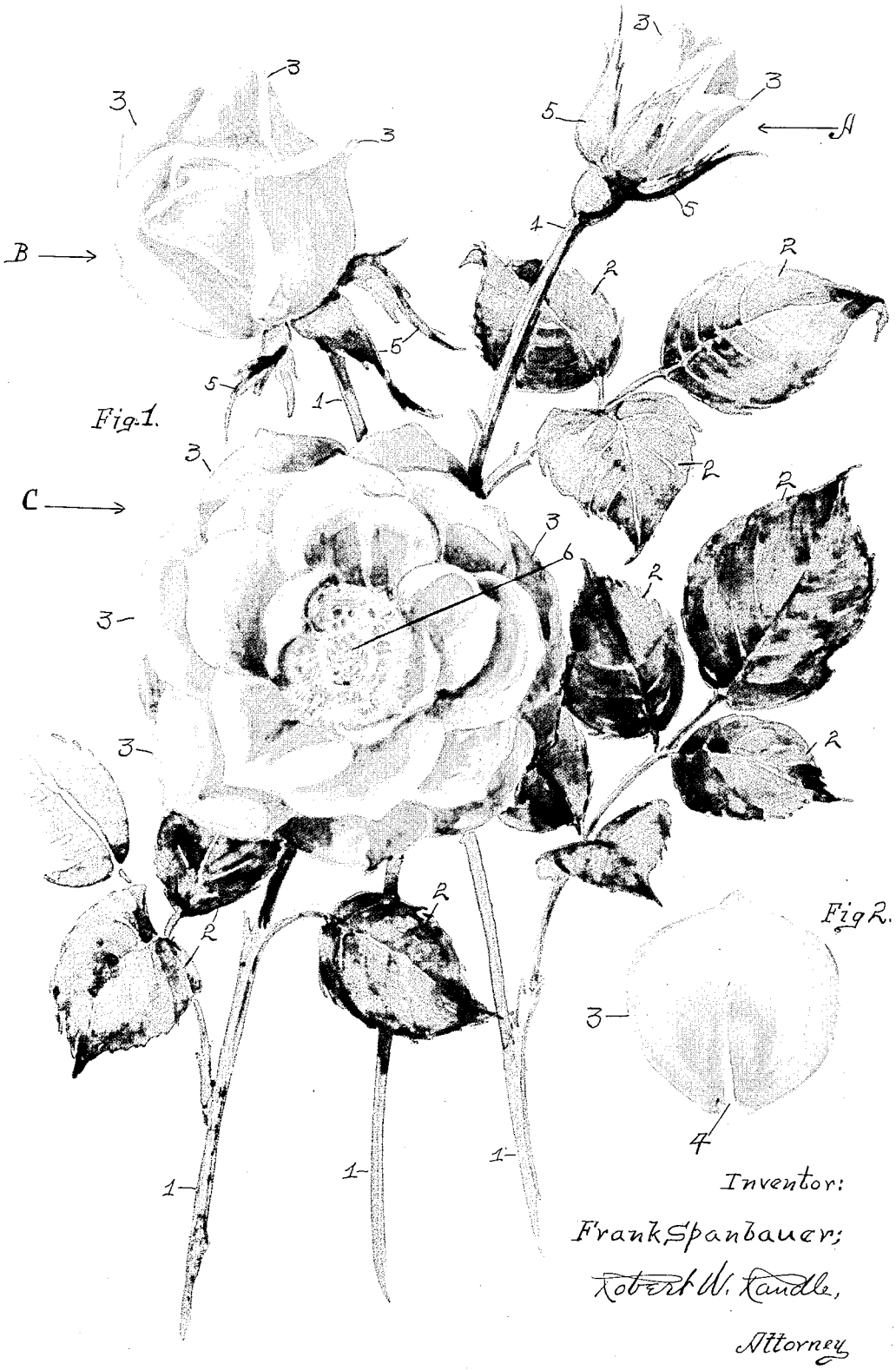
Inventor:
Frank Spanbauer;
Robert W. Landle,
Attorney Patented Oct. 13, 1931

Plant Pat. 2

UNITED STATES PATENT OFFICE

FRANK SPANBAUER, OF NORTH KANSAS CITY, MISSOURI

ROSE

Application filed July 1, 1930. Serial No. 465,160.

The object of this invention, broadly stated, is the production of a new flower, or more particularly a new and distinct variety of the species or genus "Rosa"; the same being produced and propagated by intensive cultivation, scientifically conducted, by means of hybridization and inter-crossing, in order to bring out and develop the most desirable features possible, thereby eventuating in the production of a new rose which is unique in character, highly delectable and æsthetic to one's sense of sight, as well as pleasant to one's sense of smell, which can be asexually reproduced, and in which the characteristics thereof are permanently fixed.

More specifically stated, my invention consists in the production of a new and distinct variety of rose, the same being recognizable by producing cordate, or heart-shaped, petals; emitting a high degree of fragrance, of an extremely delicate desirable quality which is unusually prolific in growth; is of strong, vigorous, and quick growth; has extra long stems; is practically free from diseases; produces more stems and a greater number of blooms to each bush; produces blooms of an unusually large size; and with a greater number of petals to each bloom; and many other desirable features are inherent therein which are not found in other roses.

My new rose is especially noticeable as predominately scarlet crimson in color, with a white streak in the center of the inner portion of the petals. My new rose is unusually hardy in growth and in disease resistance; it has a high degree of resistance against insects, blight, fungi, and atmospheric influences; being also high in ever-blooming and storage qualities, and in ease of asexual reproduction; and which retains its fragrance and beauty for an unusually long period of time.

My new rose is produced by hybridization, cross-fertilizing, and careful breeding, and it has been developed, propagated, tested, and asexually reproduced to provide a new variety having distinct characteristics which are easily distinguishable and which, it is believed, are permanently fixed and is susceptible of being asexually reproduced indefinitely upon a commercial scale.

My new rose was developed substantially as follows: The two varieties of roses used as the progenitors were the "General Jacqueminot rose", as the male member and the "Richmond rose", as the female member. From the stamens of the male member pollen was taken and placed in the stigma of the female member. From these the seed formed in the female member was sown in soil and brought forth male and female roses, which for identification only I denominate as "No. 5" being the male and "No. 1" the female. When Nos. 1 and 2 are fully open in bloom then the pollen from the stamens of No. 5, was at the proper time, placed in the stigmas of No. 1, thereby crossing No. 5 and No. 1, which produced my new rose, which is therefore a hybrid Tea rose.

My new rose was then asexually reproduced and propagated, and it has also been improved, by intercrossing and otherwise, whereby the individuality and the desirable characteristics of my rose has been greatly improved and its characteristics are fixed.

All parts of the petals of my rose are scarlet crimson in color, except at the base of the middle of the outer petals where there is a white streak extending about one-fourth of the way up. The petals of my rose are inclined to be cordate in form, thereby adding to their beauty, novelty, and individuality.

In the accompanying drawings, forming a part of this specification, I have shown my perfected rose in three stages of its natural developement, that is in blooming, the same including the bud, the partly open bloom, and the full bloom rose. The drawings also show the new features which are visible, but of course does not show the new features which are indiscernible to one's eyes.

The drawings show my rose in its natural colors, that is as near as is possible to do artificially.

In the drawings Figure 1 shows my new rose in its natural colors, in bud, in half-bloom and in full bloom.

Figure 2 is a plan view of the inner sides of one of the petals.

Letter A denotes the bud, B denotes the half-bloom; and C denotes the full bloom.

More specifically,—numeral 1 denotes stems; numeral 2 denotes leaves; numeral 3 denotes petals; numeral 4 denotes the white streak which streaks are on the inside face of the petals, or at least most of them, and which are more pronounced on the inner face of the outer petals, and in the drawings only one of them appear, and that in Fig. 2. Numeral 5 denotes the sepals forming the calyx; and numeral 6 denotes the pistil or regenerative organs.

It is to be understood that various changes may be made in the procedure, and in the details set forth, without departing from the spirit of my invention or sacrificing any of the advantages thereof which are new.

Having now fully shown and described my new rose, and the mode of its production, what I claim and desire to secure by Letters Patent of the United States, is—

A rose substantially as herein shown and described, characterized and predominantly distinguished by petals which are scarlet crimson in color, semi-double in appearance, and in which the outer petals are inclined to be cordate in shape.

In testimony whereof I have hereunto subscribed my name.

FRANK SPANBAUER.